United States Patent [19]

Matsumoto et al.

[11] Patent Number: 4,610,665
[45] Date of Patent: Sep. 9, 1986

[54] MEDICAL INSTRUMENT

[75] Inventors: Atsushi Matsumoto, Chofu; Tatsuo Suzuki, Yokohama, both of Japan

[73] Assignee: Terumo Kabushiki Kaisha, Tokyo, Japan

[21] Appl. No.: 567,790

[22] Filed: Jan. 3, 1984

[30] Foreign Application Priority Data

Jan. 18, 1983 [JP] Japan ................................. 58-5348
Mar. 7, 1983 [JP] Japan ................................. 58-35939
Oct. 22, 1983 [JP] Japan ............................... 58-196950

[51] Int. Cl.$^4$ ............................................. A61M 25/00
[52] U.S. Cl. ..................................... 604/167; 604/256
[58] Field of Search ................. 604/167, 30, 99, 169, 604/174, 175, 201, 213, 215, 237, 244, 256, 411, 905; 128/DIG. 26

[56] References Cited

U.S. PATENT DOCUMENTS

| | | |
|---|---|---|
| 3,853,127 | 12/1974 | Spademan ........................... 604/167 |
| 4,000,739 | 1/1977 | Stevens ............................... 604/167 |
| 4,143,853 | 3/1979 | Abramson . | 
| 4,177,814 | 12/1979 | Knepshield ......................... 604/167 |
| 4,412,836 | 11/1983 | Brignola ............................. 604/237 |
| 4,430,081 | 1/1984 | Timmermans ..................... 604/167 |
| 4,436,519 | 3/1984 | O'Neill ............................... 604/256 |
| 4,475,548 | 10/1984 | Muto ................................... 604/167 |
| 4,496,348 | 1/1985 | Genese et al. ..................... 604/167 |

Primary Examiner—Stephen C. Pellegrino
Assistant Examiner—Mark Rooney
Attorney, Agent, or Firm—Frishauf, Holtz, Goodman & Woodward

[57] ABSTRACT

A medical instrument comprises a main body having a path formed therethrough, through which a tubular member is insertable or drawable. A valve body is provided in the path of the main body, maintaining at least a liquid-tight state with the rod-like member, when the path is opened by the rod-like member inserted through the path, and closing the path at least in the liquid-tight state, when the rod-like member is not inserted through the path. The valve body has two end faces. The valve body is formed with a first slit openable in one of the end faces and a second slit openable in the other of the end faces. The first slit and the second slit cross each other in the valve body.

In consequence, rod-like members being of widely varied outer diameters are inserted through the path of the main body and held therein in a liquid-tight state to thereby reliably prevent blood leakage. Also, blood flow-out when the rod-like member or members are abruptly withdrawn from the path of the main body is reliably prevented. Further, a single valve body is provided so that the construction of the medical instrument can be simplified.

15 Claims, 32 Drawing Figures

MEDICAL INSTRUMENT

BACKGROUND OF THE INVENTION

1. Field of the Invention

This invention relates to medical instruments, and more particularly to a medical instrument suitable for use in a catheter introducer, a general catheter, a catheter with a balloon, an ectosomatic circulating device and the like.

2. Description of the Prior Art

There has heretofore been used a catheter introducer for medical treatment as a means for introducing rod-like members such for example as a catheter for blood-vessel contrast and the like into a blood-vessel. In a method of introducing a catheter using a catheter introducer into a blood-vessel, firstly, a hollow needle inserted therethrough with an inner needle penetrates through a skin and is introduced into the blood-vessel, subsequently, a guide wire is inserted through the hollow needle, from which the inner needle is removed, and thereafter, the hollow needle is removed and only the guide wire is left behind. Subsequently, a main body of the introducer inserted therethrough with an expander is advanced into the blood-vessel through the guide wire and thereafter, the dilator together with the guide wire, and the catheter is guided into a path in a main body so as to be insertable into the blood-vessel.

In the catheter introducer for medical treatment as described above, when the catheter is inserted into a path of the main body of the introducer and when the catheter is not inserted, in order to prevent a blood flow to the outside through the path of the main body of the introducer, it is necessary to provide a valve body in the path of the main body of the introducer.

In FIGS. 1 and 2, designated at reference numeral 1 is a catheter introducer for medical treatment, 2 a main body, 3 a cap, and 4 a catheter. In this catheter introducer 1, a first valve body 5 and a second valve body 6, which are made of an elastomeric material, are parallelly provided in a path 2A of the main body 2 in a manner to be clamped by the main body 2 and the cap 3. The first valve body 5 is provided at the central portion thereof with a round opening 5A, and makes it possible to prevent a blood leak under conditions where the catheter 4 is inserted into the path of the main body 2. The second valve body 6 is provided at the central portion thereof with a slit 6A, and makes it possible to prevent a blood leak when the catheter 4 is not inserted through the path of the main body 2.

However, a valve body assembly comprising the first valve body 5 and the second valve body 6, an outer diameter of the catheter 4 which is applicable is primarily fixed as commensurate to the round opening 5A formed on the first valve body. In consequence, when only the guide wire is inserted and held in the first valve body 5 and the second valve body 6, a blood leak cannot be prevented, and it becomes difficult to apply to a forward end flexing type catheter requiring a combination of the catheter introducer 1 with the guide wire. Furthermore, in removing the catheter 4 inserted in the main body 2, if the catheter 4 is abruptly withdrawn, then there is a possibility that the slit 6A does not immediately form a suitable closed state and a blood flow-out occurs. Furthermore, this valve body assembly, consisting of the two valve bodies including the first valve body 5 and the second valve body 6, becomes complicated in construction.

In another catheter introducer for medical treatment of the prior art, which has been proposed in Japanese Patent Application No. 178915/81(Patent Kokai(Laid-Open)No. 110262/82), such a valve body assembly is used which includes a disc-shaped first valve body having an expandable opening, by which no materials are removed, and a tubular second valve body provided with a forward end portion having sealing lips which are pressed against each other. However, the valve body assembly, being small in scope of expansion or contraction of the opening provided in the first valve body, cannot have tubular members of widely varied outer diameters inserted therethrough and held therein. Furthermore, the valve body assembly, consisting of the two valve bodies including the first valve body and the second valve body, becomes complicated in construction.

The present invention has as its object the provision of a medical instrument having a valve body having hollow rod-like members including hollow cylindrical members and/or solid columnar members of widely varied outer diameters inserted therethrough and held therein in a liquid-tight state, capable of immediately forming a proper closed state when the rod-like member or members are withdrawn, and having a simple construction.

SUMMARY OF THE INVENTION

To above end, the present invention contemplates that, in a medical treatment device comprising a main body of a medical instrument provided therethrough with a path, through which a rod-like member is insertable or drawable, and a valve body provided in said path of the main body, maintaining a seal around and at least a liquid-tight state with the rod-like member when opened by the rod-like member, and closing the path at least in the liquid-tight state when said rod-like member is absent from the path. The valve body has two end faces in the direction of the path, and is formed with a first slit openable in one of the end faces and a second slit openable in the other of the end faces, the first slit and the second slit crossing each other in the valve body, and the rod-like member being insertable or drawable at the cross section of the slits.

To the above end, the present invention contemplates that the main body has a flexible tube having at one end thereof an opening communicated, and the path and formed at the other end there of with another opening provided with a means in which a plurality of flow courses can be switched to one another.

To the above end, the present invention contemplates that the main body comprises a tubular member, a tubular member hub solidly secured to the proximal end of said tubular member, having a path communicated with a path formed in said tubular member and provided in said path with said valve body; a dilator tube insertable or drawable through said paths both in said tubular member and said tubular member hub having the forward end portion thereof positioned at the other end of said tubular member when inserted; and a dilator hub solidly secured to the proximal end of said dilator tube and capable of being coupled to said tubular member hub.

The present invention also contemplates that the main body is provided at one end portion thereof with a catheter communicated with said path and is provided at an opening portion of the proximal end thereof with a valve body.

The present invention further contemplates that the main body is a tubular member and at least one end thereof is a connector which is connected to a tubular portion of another medical instrument.

The present invention still further contemplates that the main body has at least two opening end portions connected to opening portions of tubes; respectively said opening end portions are communicated with each other through a flow course; and a guide portion having a path communicated with said flow course, for guiding the insertion of said rod-like members to a valve body provided in said path.

The present invention also contemplates that the main body includes a catheter having a main path and a balloon provided on the peripheral portion at the forward end of said catheter; said catheter has an auxiliary path extending from the proximal end to the forward end thereof and communicated with a space in said balloon; a balloon expanding liquid is made pourable into a space in said balloon by means of a pouring device; and said valve body is provided at an opening portion of said auxiliary path.

The present invention also contemplates that the main body comprises a tubular member, a tubular member hub solidly secured to one end of said tubular member and having a path communicated with the interior of said tubular member, an inner needle passing through a path of said tubular member, made insertable or drawable into said tubular member and having a needle point positioned at the other end of said tubular member when inserted in said tubular member, and an inner needle hub capable of being coupled to said tubular hub and solidly secured to the proximal end of said inner needle; and said valve body is provided in the path of said tubular member hub.

The present invention further contemplates that the valve body is a disc-like gasket and is made of a flexible and elastomeric material.

The present invention still further contemplates that, in the valve body, the first slit comprises a plurality of slit portions crossing one another, the second slit comprises a plurality of slit portions crossing one another, and the first slit portions and the second slit portions cross each other at a single positon in the inner sides thereof.

The present invention still further contemplates that, in the valve body, the first slit comprises a plurality of slit portions not crossing one another, the second slit comprises a plurality of slit portions not crossing one another, and the first slit and the second slit cross each other at a plurality of positions in the inner sides thereof.

The present invention further contemplates that the valve body has at least one convex end face.

The present invention still further contemplates that the slit is formed axially to a valve body and the main body is cylindrical.

The rod-like members to be inserted according to the present invention include a catheter, a guide wire, a syringe tip, a needle, etc., for example.

DESCRIPTION OF THE PREFERRED EMBODIMENTS OF THE INVENTION

Figure 1:
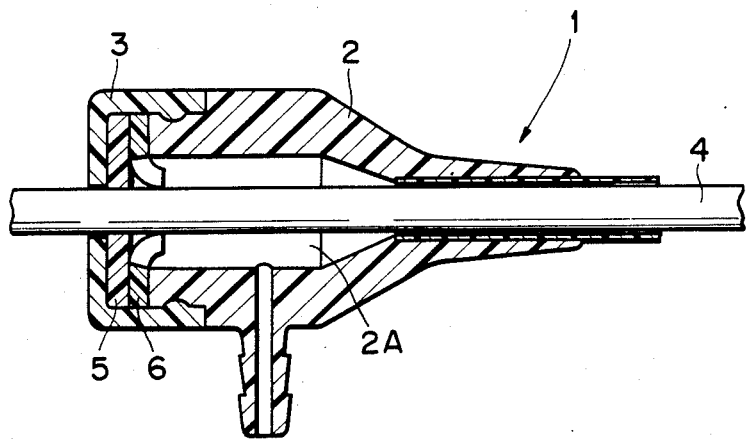
FIG. 1 is a sectional view showing the catheter introducer for the medical instrument, to which the valve body assembly according to the prior art is applied.
Figure 2:
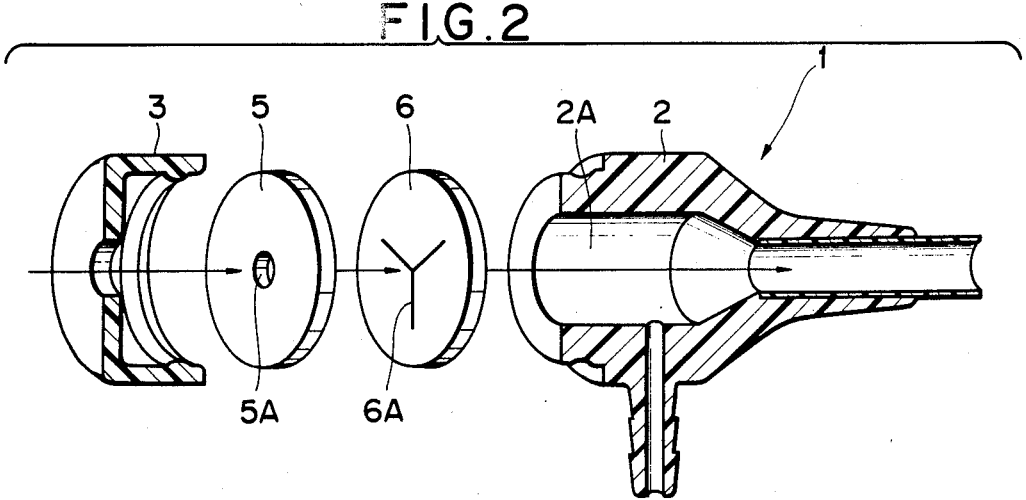
FIG. 2 is a disassembled perspective view of FIG. 1.
Figure 3:
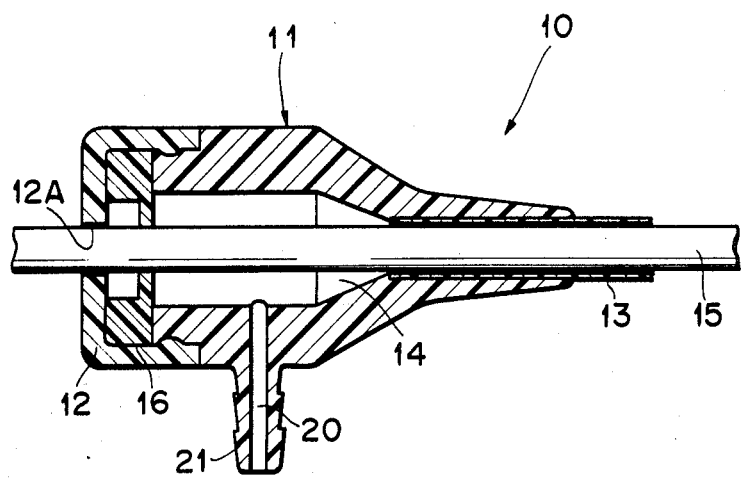
FIG. 3 is a sectional view showing the catheter introducer for the medical instrument embodying the present invention.
Figure 4:
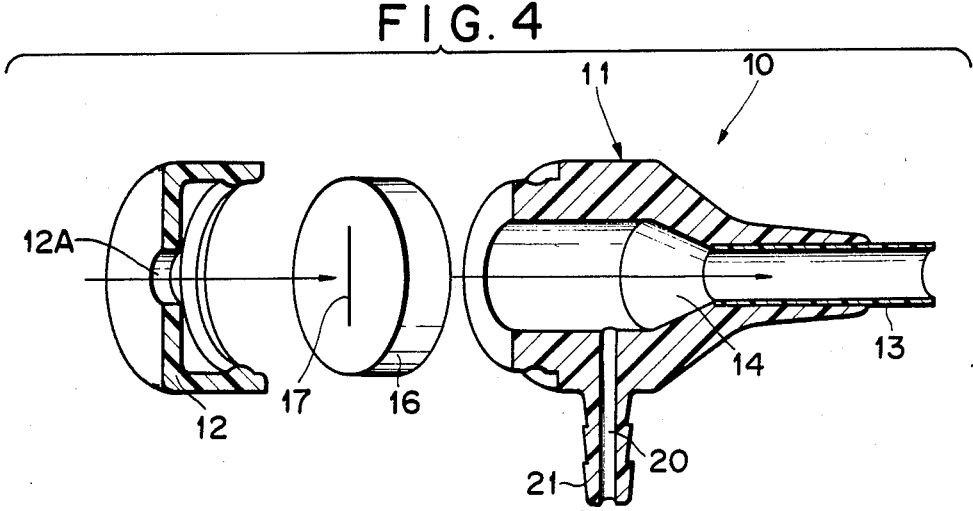
FIG. 4 is a disassembled perspective view of FIG. 3.

FIG. 3 is the sectional view showing the catheter introducer for a medical instrument, to which the first embodiment of the valve body according to the present invention is applied, and FIG. 4 is the disassembled perspective view of FIG 3. The catheter introducer for the medical instrument 10 comprises a substantially cylindrical main body 11 and a cap 12 coupled to one end of the main body 11 and having an opening 12A. A flexible tube 13 is integrally connected to the tapered end of the main body 11. An axial path or passage 14 is formed in the main body 11 and the flexible tube 13. A catheter 15 can be inserted through the path or passage 14. Provided at one end portion of the main body 11 in a state of being clamped between the main body 11 and the cap 12 is a single disc-shaped valve body 16 as being an embodiment of the present invention, which forms a liquid-tight state in cooperation with the catheter 15 inserted through the path 14 and closes the path 14 when the catheter 15 is not inserted.

The valve body 16 is made of a flexible and elastomeric material including a synthetic rubber such as a silicone rubber, urethane rubber or a fluororubber, and a natural rubber, etc.

Figure 5A:
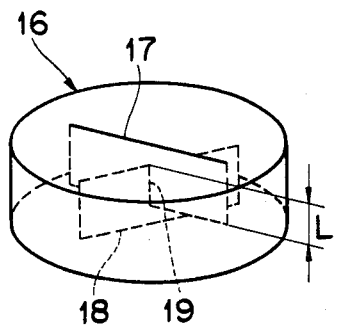
FIG. 5(A) is a perspective view showing the valve body in FIG. 3 being taken out.
Figure 5B:
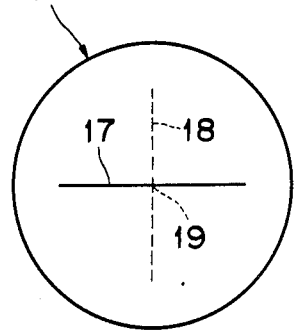
FIG. 5(B) is a plan view showing the valve body.
Figure 5C:
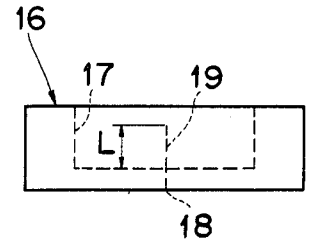
FIG. 5(C) is a side view showing the valve body.
Figure 6:
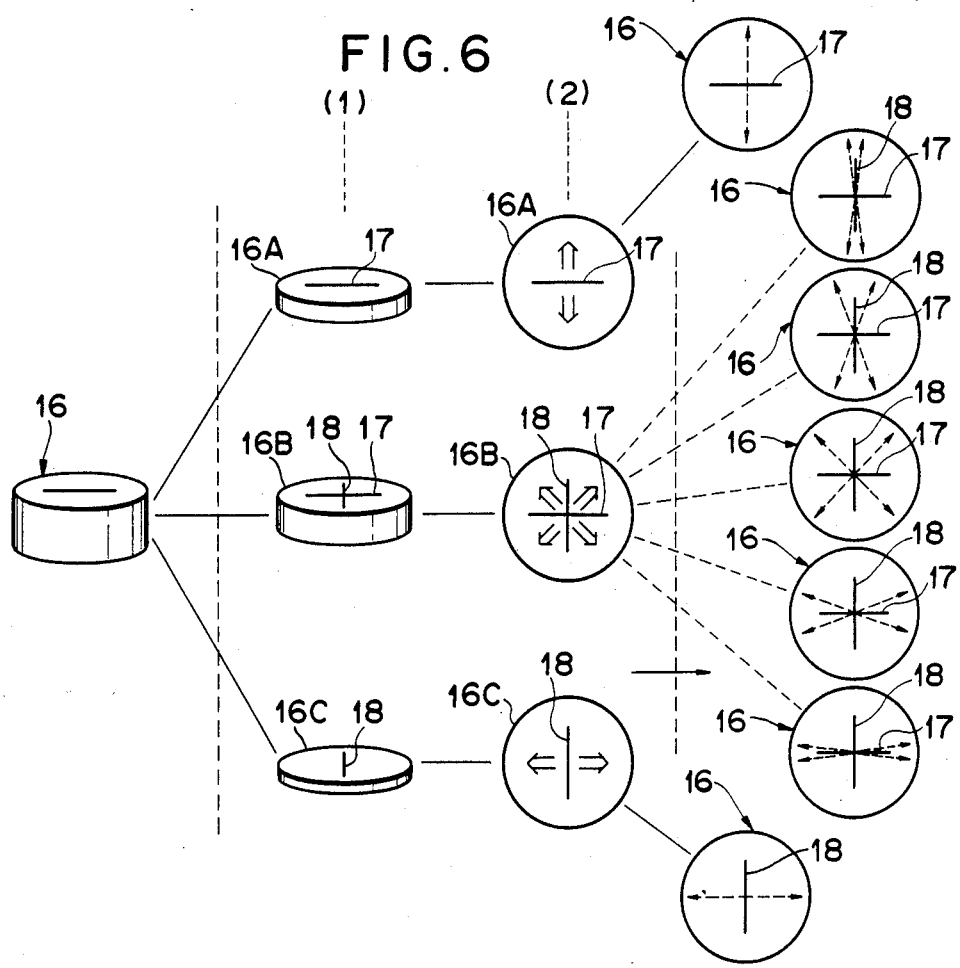
FIG. 6 is an explanatory view showing directions of deformation of the slits provided in the valve body.
Figure 7:
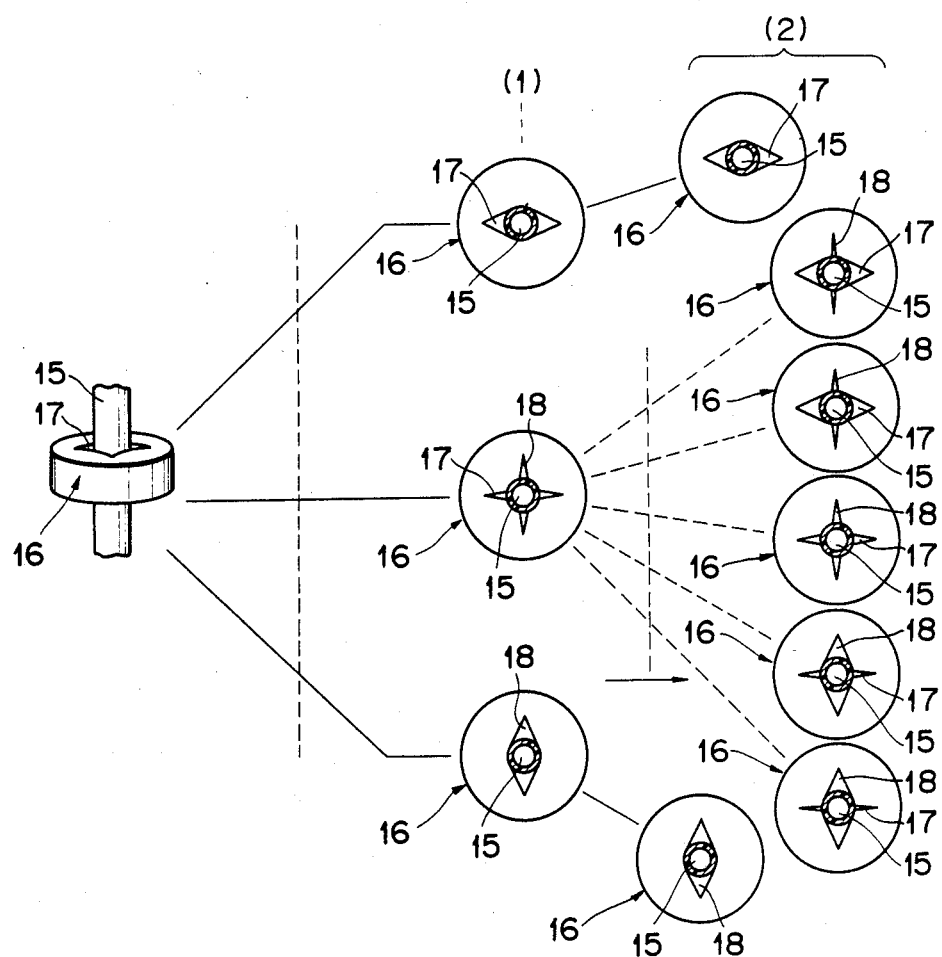
FIG. 7 is an explanatory view showing the shapes of openings in the slits provided in the valve body.

As shown in FIGS. 5(A) and 5(C), the valve body 16 is formed therein in a suitable method with a first slit 17 openable to one of the end faces thereof and a second slit 18 openable to the other of the end faces thereof. The first slit 17 and the second slit 18 cross each other at the inside of the valve body 16. The term "cross" means that the slits are combined together alternately, whereby the slits formed from opposite end faces partially coincide with each other at the crossing portion, so that the rod-like members are insertable. In addition, the angle of crossing need not necessarily be a right angle. More specifically, the first slit 17 and the second slit 18 form a crossing portion 19. In consequence, the catheter 15 is made passable through the first slit 17, the second slit 18 and the crossing portion 19 formed therebetween under an elastic deformation of the valve body 16. FIG. 6 is the explanatory view showing the direction of deformation of the first slit 17 and the second slit 18 when the catheter 15 is inserted through the valve body 16. FIG. 7 is the explanatory view showing the shapes of openings in the first slit 17 and the second slit 18 when the catheter 15 is inserted through the valve body 16. If the valve body 16 is sliced into three characteristic portions in the axial direction thereof, including a portion having therein only the first slit 17, a portion having therein a crossing portion 19 and a portion having therein only the second slit 18, then there exist three portions 16A through 16C as shown in (1) of FIG. 6. If, in the valve body 16, three separate portions as shown at the 16A through 16C are merely superimposed on one another, then the directions of deformation of the slits 17 and 18 when the insertion is about to be made become ones as indicated by arrow marks in (2) of FIG. 6, and shapes of openings of the slits 17 and 18 after the insertion become ones shown in (1) if FIG. 17. However, since the valve body 16 is originally an integral body by itself, each of the sliced portions is subject to the influences from the other portions adjacent thereto, the directions of deformation of the slits 17 and 18, when the catheter 15 is about to be inserted, are continuously varied inside the valve body 16 along the axial direction thereof as indicated by arrow marks in (3) of FIG. 6, and the shapes of openings of the slits 17 and 18 after the insertion becomes ones shown in FIG. 7. More specifically, the surroundings of the catheter 15 inserted through the valve body 16 are continuously pressed by the slits 17 and 18 along the axial direction of the valve body 16 with no gaps being formed even when the outer diameter of the catheter 15 is comparatively small of comparatively large. Since the valve body 16 is made of the flexible and elastomeric material as aforesaid, the slits 17 and 18 come into close surface-to-surface contact with the outer peripheral portion of the catheter 15, to thereby form a reliable liquid-tight or air-tight state between the catheter 15 and the valve body 16. In addition, a distance L formed by the crossing portion 19 between the first slit 17 and the second slit 18 is determined in accordance with the maximal outer diameter of the catheter 15 to be inserted into the valve body 16.

Figure 8:
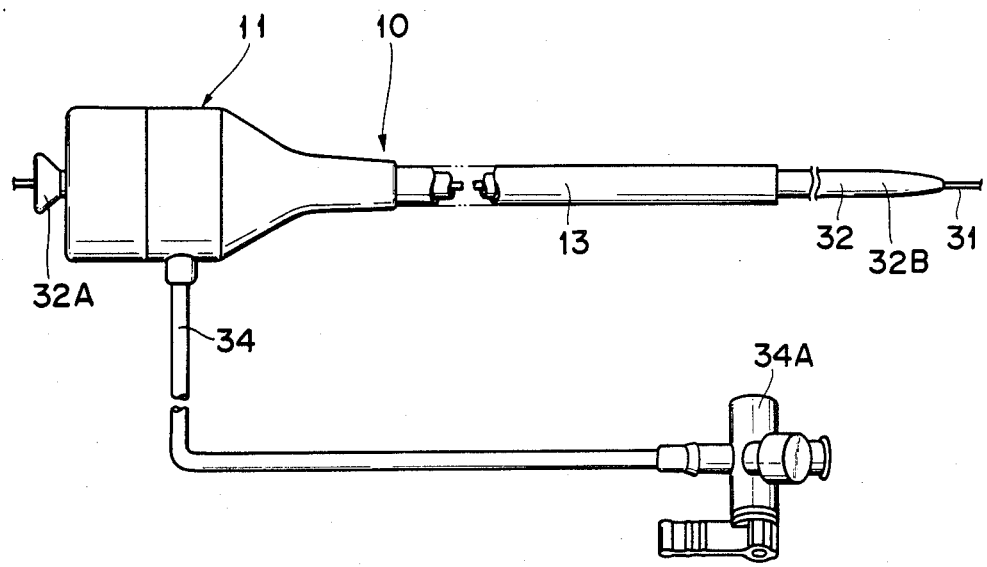
FIG. 8 is an explanatory view showing the state where the guide wire and a dilator are inserted through the catheter introducer for a medical instrument.

In addition, a above-described catheter introducer 10 for the medical instrument is integrally formed thereon with a connecting portion 21 forming a path 20 communicated with the path 14. The connecting portion 21 introduces heparin physiological salt-water, etc., into the catheter introducer 10 for a medical instrument through the path 20, to thereby make it possible to prevent a thrombus from occurring in the path 14, at the border between the path 14 and the catheter 15 as so on. In addition, as shown in FIG. 8, a feed tube 34, such as a side tube, is connected at one end thereof to the connecting portion 21 and at the other end thereof to a three-way stop cock 34A, whereby the aforesaid heparin physiological salt-water can be fed to the path 14 via a syringe connected to this three-way stop cock 34A. Additionally, the three-way stop cock need not necessarily be limited to this one shown, but, such a stop cock is adoptable that a plurality of flow courses such as two-way or four-way can be switched from one another.

Figure 9:
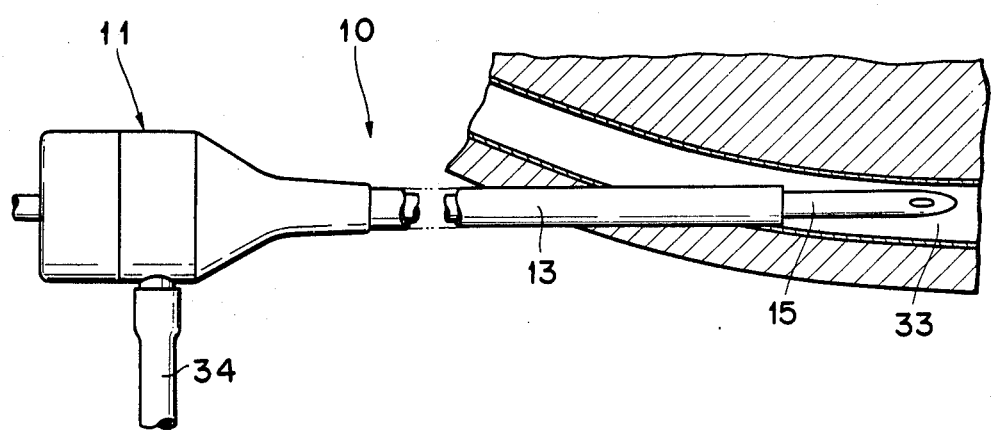
FIG. 9 is an explanatory view showing the state of use of the catheter introducer for the medical instrument.

Description will hereunder be given of the method of using the catheter introducer 10 for the medical instrument, provided with the valve body 16 with reference to FIGS. 8 and 9. Prior to the use of the catheter introducer 10 for the medical instrument, a hollow needle having inserted therethrough an inner needle penetrates through a skin and is introduced into a blood-vessel, a guide wire 31 is inserted through the hollow needle, from which the inner needle has been removed, and thereafter, the guide wire 31 remains after the removal of the hollow needle. Subsequently, as shown in FIG. 8, a dilator 32, which has been inserted through the path 14 of the catheter introducer 10 for the medical instrument, is coupled, covering the guide wire 31. The dilator 32 comprises a dilator hub 32A couplingly connectable to the main body 11 and a dilator tube 32B insertable into the main body 11 and the flexible tube 13. Subsequently, the forward end portion of the dilator tube 32B of the dilator 32 is inserted through the wall of a blood-vessel, and the flexible tube 13 of the catheter introducer 10 of the medical instrument is introduced into a blood-vessel 33, dilating the hole penetrating the blood-vessel wall. Subsequently, while heparin physiological salt-water is fed into the path 14 via the feed tube 34 connected to the connecting portion 21 and the three-way stop cock 34A, the dilator 32 and the guide wire 31 are removed. While the guide wire 31 and the dilator 32 are inserted through the path 14 of the catheter introducer 10 for the medical instrument as described above, the valve body 16 is in close contact with the outer peripheral portion of the dilator 32 with no gaps being formed, so that the blood flowout can be prevented. While only the flexible tube 13 of the catheter introducer 10 for the medical instrument is introduced into the blood-vessel 33 and remains therein after the guide wire 31 and the dilator 32 are removed from the path 14 of the catheter introducer 10 for the medical instrument, the valve body 16 completely closes the first slit 17 and the second slit 18, thus preventing the blood flowout. In addition, in the valve body 16, each of the slits 17 and 18 is not open to the end face at the other side, whereby pressure resistance to the blood pressure acting on the end faces of the valve body 16 is high, so that a stably closed state can be maintained without being deformed by the blood pressure.

Subsequently, the catheter 15 is introduced through an opening 12A of the cap 12 and pentrates through the slits 17 and 18 of the valve body 16. The catheter 15 penetrates through the main body 11, is guided to the flexible tube 13 and reaches the blood-vessel 33. While the catheter 15 is inserted through the path 14 of the catheter introducer 10 for the medical instrument as described above, the valve body 16 is in close contact with the outer peripheral portion of the catheter 15 with no gaps being formed, whereby a liquid-tight state is maintained, so that the blood leak can be prevented. In addition, when the catheter 15 reaches a suitable position, a desired medical working such as a blood contract X-ray photographing can be performed.

Subsequently, when the catheter 15 is removed from the catheter introducer 10 for the medical instrument, the catheter 15 is withdrawn from the slits 17 and 18 of the valve body 16, and sumultaneously, the slits 17 and 18 form a perfectly closed seal, thus preventing the blood flowout. In addition, since each of the slits 17 and 18 of the valve body 16 is open only to an end face at one or the other side of the valve body 16, the force of restitution to the closed state is strong when the catheter 15 is removed, and no conversly opening action at the end face opposite thereto is made.

In addition, according to the above embodiment, the slits 17 and 18 of the valve body 16 can come into close contact with any one of the catheters widely varied in outer diameter. In consequence, only the guide wire can be inserted into the catheter introducer 10 for the medical instrument, which is in a remaining state, and held therein. Further, it is possible to introduce into the blood-vessel the catheter along with the catheter introducer 10 and the guide wire in the liquid-tight state.

Figure 10:
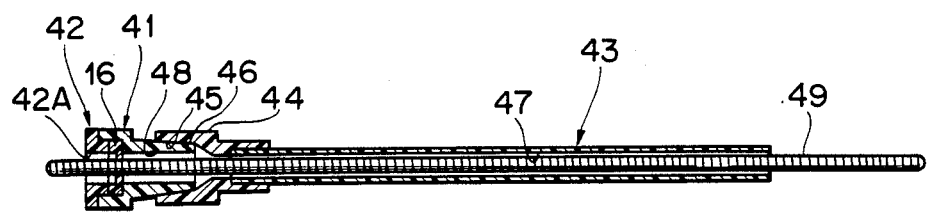
FIG. 10 is a sectional view showing the catheter embodying the present invention.
Figure 11:
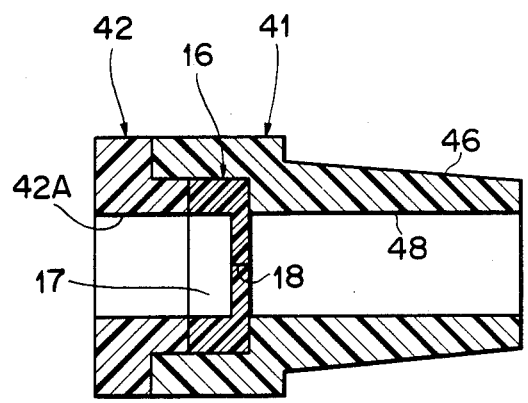
FIG. 11 is a sectional view showing the essential portions in FIG. 10 being taken out.

FIG. 10 is the sectional view showing the catheter provided at the opening disposed at the proximal end of the valve body 16 as another example, to which the valve body 16 is applied, and FIG. 11 is the sectional view showing the essential portions thereof being taken out.

In this example of application, the valve body 16 is clamped between a plug 41 and a cap 42 coupled to one end portion of the plug 41. The plug 41 is provided with a tapered outer surface 46 for being detachably coupled thereto with a tapered inner surface 45 of an opening of a hub 44 constituting a proximal end portion of a blood-vessel catheter 43, which can be introduced into the blood-vessel and remain therein, and further, provided with a path 48 communicated with a path 47 of the blood-vessel catheter 43. The cap 42 is formed with a path 42A. Additionally, designated at 49 is a guide wire.

Description will hereunder be given of the method of using the aforesaid blood-vessel catheter 43 provided with the valve body 16. Firstly, prior to the use of the valve body 16 and the blood-vessel catheter 43, the hollow needle, having inserted therethrough the inner needle penetrates the skin and is introduced into the blood-vessel. Thereafter, the guide wire 49 is inserted through the hollow needle, from which the inner needle has been removed, and thereupon, the hollow needle is removed, leaving the guide wire behind. Subsequently, in a state where the plug 41 provided with the valve body 16 is coupled to the hub 44 of the blood-vessel catheter 43, the guide wire 49 is coupled into the path 47 of the blood-vessel catheter 43, and the blood-vessel catheter 43 is introduced into the blood-vessel, while being guided by the guide wire 49. When the blood-vessel catheter 43 is introduced into the blood-vessel under the guidance of the guide wire 49, the blood from the blood-vessel flows into the path 47 of the blood-vessel catheter 43. However, since the plug 41 having the valve body 16 is coupled to the hub 44 provided at the proximal end of the blood-vessel catheter 43 and the first slit 17 and the second slit 18 of the valve body 16 are kept in the closed state, the blood is prevented from flowing out of the opening disposed at the proximal end of the blood-vessel catheter 43. Additionally, since each of the slits 17 and 18 in the valve body 16 are not open to the end face opposite thereto, the pressure resistance of the valve body 16 to the blood pressure acting on the end faces of the valve body 16 is high, so that the slits can be held in a stably closed state, without being deformed by the blood pressure.

When the introduction of the blood-vessel catheter 43 into the blood-vessel is progressed, the valve body 16 secured to the opening at the proximal end of the blood-vessel catheter 43 penetrates through the outer end portion of the guide wire 49 as shown in FIG. 10. However, the slits 17 and 18 of the valve body 16 come into close surface-to-surface contact with the outer peripheral portion of the guide wire 49 with no gaps being formed, whereby the liquid-tight state is maintained, so that the blood leak can be prevented.

When the forward end portion of the blood-vessel catheter 43 reaches a predetermined position in the blood-vessel as described above, the guide wire 49 is removed from the path 47 of the blood-vessel catheter 43. In addition, to remove the guide wire 49 from the blood-vessel catheter 43, the guide wire 49 is withdrawn from the slits 17 and 18 of the valve body 16, and simultaneously, the slits 17 and 18 form a perfectly closed seal, so that the blood flowout can be prevented. Since each of the slits 17 and 18 of the valve body 16 is open to only one or the other of the end faces, the force of restitution to the closed state is strong when the guide wire 49 is removed, and no conversely opening action at the end face opposite thereto is made. Furthermore, while the guide wire 49 is removed from the path 47 of the blood-vessel catheter 43 and only the blood-vessel catheter 43 remains in the blood-vessel, the valve body 16 perfectly closes the slits 17 and 18, respectively, so that the blood flowout can be prevented.

Subsequently, to pour a blood-vessel contrast agent into the blood-vessel through path 47 of the blood-vessel catheter 43, a pour tip, penetrating through the valve body 16, is provided at the forward end of a syringe for the blood-vessel catheter 43. When the pour tip of the syringe penetrates through the valve body 16 as described above, the slits 17 and 18 of the valve body 16 come into close surface-to-surface contact with the outer periphery of the pour tip with no gaps being formed, whereby the liquid-tight state is maintained, so that the blood leak can be prevented. Furthermore, when the pour tip of the syringe is removed from the valve body 16, the slits 17 and 18 of the valve body 16 immediately form a perfectly closed seal, so that the blood flowout can be prevented. In addition, the slits 17 and 18 of the valve body 16 come into close surface-to-surface contact with the outer periphery of the rod-like member with no gaps being formed, even when the rod-like member to be inserted is comparatively small or comparatively large in diameter, so that the slits can be in close contact with both the guide wire 49 and the pour tip of the syringe, which are different in diameter from each other, in the liquid-tight state.

Upon completion of the pouring of the blood-vessel contrast agent, the pour tip of the syringe is removed from the valve body 16, the guide wire 49 is inserted again through the valve body 16 and the blood-vessel catheter 43, and the blood-vessel catheter 43 is removed from the blood-vessel along with the guide wire 49, thus completing the whole working of the blood-vessel contrast.

Figure 12:
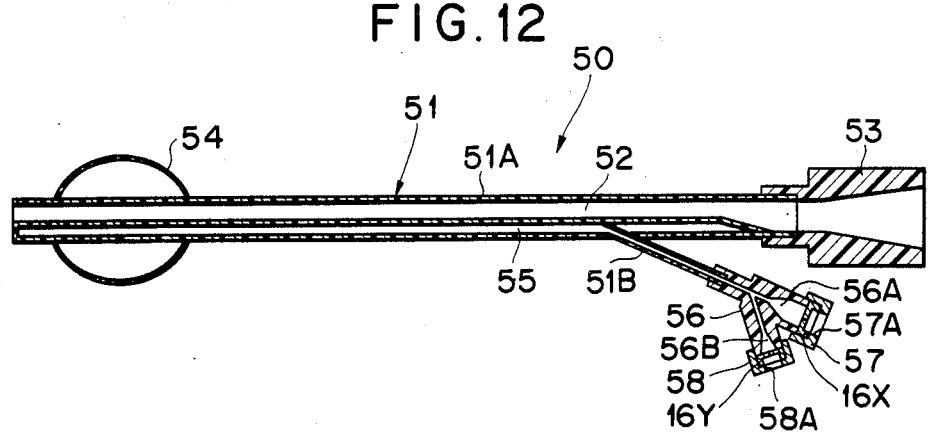
FIG. 12 is a sectional view showing the catheter with a balloon embodying the present invention.
Figure 13:
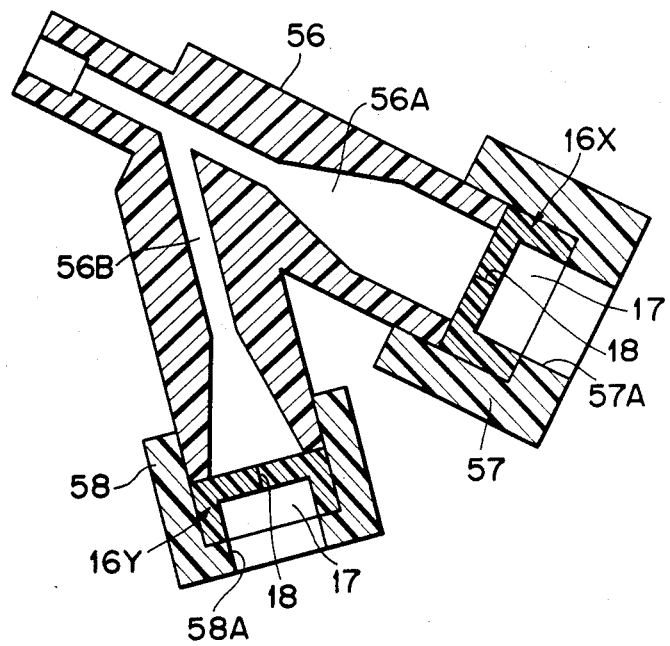
FIG. 13 is a sectional view showing the essential portions in FIG. 12 being taken out.

FIG. 12 is the sectional view showing the catheter with a balloon, provided with the valve body 16X and 16Y having the arrangement identical with that of the valve body 16 as a further example of application of the valve body 16. FIG. 13 is the sectional view showing the essential portions thereof being taken out. A main body 51 of a catheter 50 with a balloon comprises a flexible straight portion 51A and a branch portion 51B branchingly provided at the proximal end portion of the straight portion 51A. The straight portion 51A has a main path 52 penetrating through the straight portion 51A from the proximal end to the forward end thereof, and the main path 52 can receive therein a guide wire capable of introducing the catheter 50 with a balloon into the blood-vessel and can allow an agent or the like to circulate therethrough. In addition, a main hub 53 is secured to the proximal end portion of the straight portion 51A.

A balloon 54 made of an elastomeric material, which is expandable from a shrunk state, is provided on the outer peripheral portion of the forward end of the straight portion 51A. The straight portion 51A and the branch portion 51B of the main body 51 are formed with an auxiliary path 55 communicating the proximal end of the branch portion 51B with an internal space of the balloon 54. The branch portion 51B of the main body 51 is connected thereto with a Y-shaped auxiliary hub 56, and the auxiliary hub 56 is a first auxiliary path 56A and a second auxiliary path 56B, which are communicated with the auxiliary path 55. Secured to the opening at the proximal end of the first auxiliary path 56A in the auxiliary hub 56 is a valve body 16X which can receive therein a small diameter tube for the exhaust gas. Secured to the opening at the proximal end of the second auxiliary path 56B is a valve body 16Y for receiving therein a syringe capable of pouring a liquid for expanding the balloon. In addition, the aforesaid valve bodies 16X and 16Y are held by caps 57 and 58, which are coupled to the auxiliary hub 56. Furthermore, the caps 57 and 58 are formed therethrough with paths 57A and 58A, respectively.

Description will hereunder be given of the method of using the catheter 50 with the balloon, provided with the valve bodies 16X and 16Y. Firstly, prior to the use of the catheter 50 with the balloon, the hollow needle, having inserted therethrough the inner needle, penetrates the skin and is introduced into the blood-vessel. Thereafter, the guide wire is inserted through the hollow needle, from which the inner needle has been removed, and thereupon, the hollow needle is removed, leaving the guide wire behind. The catheter introducer for the medical instrument is inserted through the utilization of this guide wire. Subsequently, the guide wire is couple into the main path 52 of the catheter 50 with the balloon. The catheter 50 with the balloon is introduced into the blood-vessel under the guidance of the guide wire, and the balloon 54 being in the shrunk state is led to a predetermined position where the balloon 54 is to be expanded.

Subsequently, the small diameter tube for the exhaust gas is inserted through the path 57A of the cap 57, the slits 17 and 18 of the valve body 16X and the first auxiliary path 56A, and the forward end portion thereof is inserted through the auxiliary path 55 to a position where the balloon 54 is provided. Subsequently, the syringe capable of pouring the liquid for expanding the balloon such as physiological salt-water, is inserted through the path 58A of the cap 58, and slits 17 and 18 of the valve body 16Y. The liquid for expanding the balloon is poured into the auxiliary paths 55, 56A and 56B by use of the syringe and air in the auxiliary paths 55, 56 and 56B is discharged to outside via the small diameter tube. When the liquid for expanding the balloon is poured into the auxiliary paths 55, 56A and 56B, the slits 17 and 18 of the valve bodies 16X and 16Y come into close surface-to-surface contact with the outer periphery of the small diameter tube and the syringe with no gaps being formed, whereby the liquid-tight seal is maintained, so that the liquid for expanding the balloon can be prevented from leaking.

After air in the auxiliary paths 55, 56A and 56B is discharged as described above, the small diameter tube is removed from the auxiliary paths 55 and 56A. Thereafter, the liquid for expanding the balloon is continuously poured into the auxiliary paths 55, 56A and 56B by use of the syringe. After the balloon 54 is expanded to a state of a predetermined degree of expansion only by the liquid for expanding the balloon, the syringe is removed, and a predetermined medical working can be performed by the balloon 54 formed into the state of expansion. To remove the small diameter tube and the syringe as described above, the small diameter tube and the syringe are withdrawn from the slits 17 and 18 of the valve bodies 16X and 16Y, and simultaneously, the slits 17 and 18 form the perfectly closed state, so that the liquid for expanding the balloon can be prevented from blowing out. Since each of the slits 17 and 18 of the valve body 16X on 16Y is open only to one or the other of the end faces, the force of restitution to the closed state is strong when the small diameter tube or the syringe is removed, and no conversely opening action at the end face opposite thereto can be made. Furthermore, in each of the valve bodies 16X and 16Y, from which the small diameter tube or the syringe is removed, each of the slits 17 and 18 is open to only one or the other of the end faces, whereby the force of restitution to the closed state is strong when the small diameter tube or the syringe is removed, and no conversely opening action at the end face opposite thereto is made. Further still, in each of the valve bodies 16X and 16Y, from which the small diameter tube or the syringe is removed, each of the slits 17 and 18 is open to only one or the other of the end faces, whereby the pressure resistance to the pressure of the liquid for expanding the balloon acting on the end face of the valve body 16X or 16Y is high, so that a stably closed state can be maintained with the slits not being deformed by the pressure of the liquid for expanding the balloon.

In addition, the slits 17 and 18 of the valve bodies 16X and 16Y come into close surface-to-surface contact with the outer periphery of the small diameter tube or the syringe with no gaps being formed, even when the small diameter tube or the syringe is comparatively small or comparatively large in outer diameter, so that slits can be in close contact with the small diameter tube or the syringe differing in outer diameter from each other, in the liquid-tight state.

Figure 14:
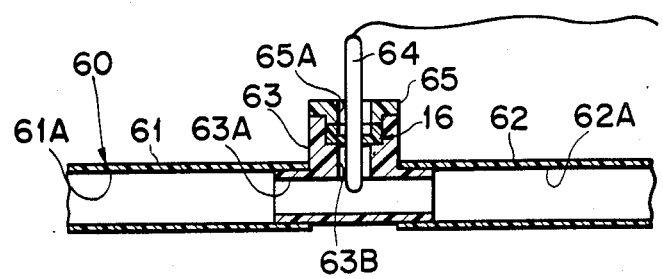
FIG. 14 is a sectional view showing an ectosomatic circulating system embodying the present invention.
Figure 15:
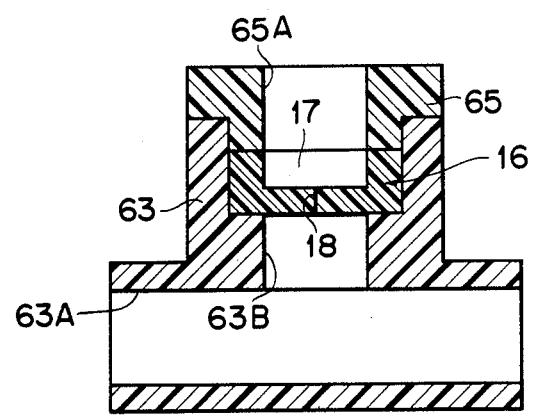
FIG. 15 is a sectional view showing the essential portions in FIG. 14 being taken out.

FIG. 14 is the sectional view showing a circulation piping portion of the ectosomatic circulating system provided with a detector installed construction using the valve body 16 as a still further example of the valve body 16, and FIG. 15 is the sectional view showing the portion of the detector installed construction being taken out. The ectosomatic circulation system 60 comprises a first piping 61 connected to a vein of a human body for example, a second piping 62 connected to an artery of the human body and a connecting piping 63 interposed therebetween. The aforesaid pipings 61, 62 and 63 have paths 61A, 62A and 63A interconnecting therebetween, respectively, constituting a circulating piping therebetween. Additionally, an artificial lung, a blood pump and the like are disposed at an intermediate portion, not shown, of the first piping 61 or the second piping 62. The connecting piping 63 has an insertion path 63B making a detector 64 insertable into the path 63A, the insertion path 63B perpendicularly intersecting the path 63A. At an opening of the insertion path 63B, there is provided the valve body 16 defining the interior and the exterior of the circulation piping, making the detector insertable into the paths 63A and 63B and being closed when the detector 64 is not inserted. In addition, the valve body 16 is positioned at the opening of the insertion path 63B in a state of being clamped between the connecting piping 63 and a cap 65 coupled to the connecting piping 63. The cap 65 is formed with a path 65A making the detector 64 insertable thereinto.

Description will hereunder be given of the method of using the ectosomatic circulating system 60 provided with the valve body 16.

If the ectosomatic circulation system 60, into which the artificial lung, the blood pump and the like are inserted, is connected to the human body, then the flow of blood occurs in the paths 61A through 63A of the first piping 61, second piping 62 and connecting piping 63. Since the valve body 16 is provided in the insertion path 63B of the connecting piping 63 and the second slit 18 is in the closed state, the blood is prevented from flowing out through the insertion path 63B of the connecting piping 63. In addition, in the valve body 16, each of the slits 17 and 18 is open only to one or the other of the end faces of the valve body 16, whereby the pressure resistance of the valve body 16 to the blood pressure acting on the end faces thereof in high, or that a stably closed state can be maintained with the slits not being deformed by the blood pressure.

To inspect whether or not a proper gas exchange is performed in the blood flowing through the ectosomatic circulating system 60, a detector 64 selected depending upon the inspection items inserted into the insertion path 63B and the path 63A of the connecting piping 63, penetrating through the path 65A of the cap 65 and the slits 17 and 18 of the valve body 16, so that partial oxygen pressure, partial carbon dioxide pressure, pH and the like in the blood can be continuously detected. The slits 17 and 18 of the valve body 16 come into close surface-to-surface contact with the outer periphery of of the detector 64 with no gaps being formed, whereby the liquid-tight state is maintained, so that the blood leak can be prevented.

Upon completion of a desired detection working by means of the detector 64, or when necessity arises for replacement of the detector 64 with new one due to the adhesion of thrombus and the like to the detector 64 positioned inside the connecting piping 63, the detector 64 is withdrawn from the slits 17 and 18 of the valve body 16. Upon withdrawal of the detector 64, the slits 17 and 18 of the valve body 16 form a perfectly closed seal, so that the blood flowout can be prevented. In addition, each of the slits 17 and 18 of the valve body 16 is open only to one or the other of the end faces of the valve body 16, whereby the force of restitution to the closed state is strong when the detector 64 is withdrawn, and no conversely opening action at the end face opposite thereto is made.

By use of the aforesaid ectosomatic circulating system 60, it becomes possible to allow the detector 64 to remain in the connecting piping 63, so that partial oxygen pressure, partial carbon dioxide pressure, pH and the like in the blood can be continuously detected and a patient can be secured in safety. The detector 64 can be installed in the connecting piping 63 after the ectosomatic circulating system 60 is set up for the patient, whereby handling of the piping system is not complicated. The detector 64 can be readily withdrawn from the connecting piping 63 during the process of ectosomatic circulation, so that the detector 64 can be quickly and easily replaced with new one when the thrombus and the like adhere thereto for example. Since the slits 17 and 18 come into close surface-to-surface contact with the inserted detector 64 with no gaps being formed, even when the detector is comparatively small or comparatively large in outer diameter, the slits 17 and 18 can be in close contact with any one of the detectors 64 differing in diameter from one another, forming a liquid-tight seal.

Figure 16:
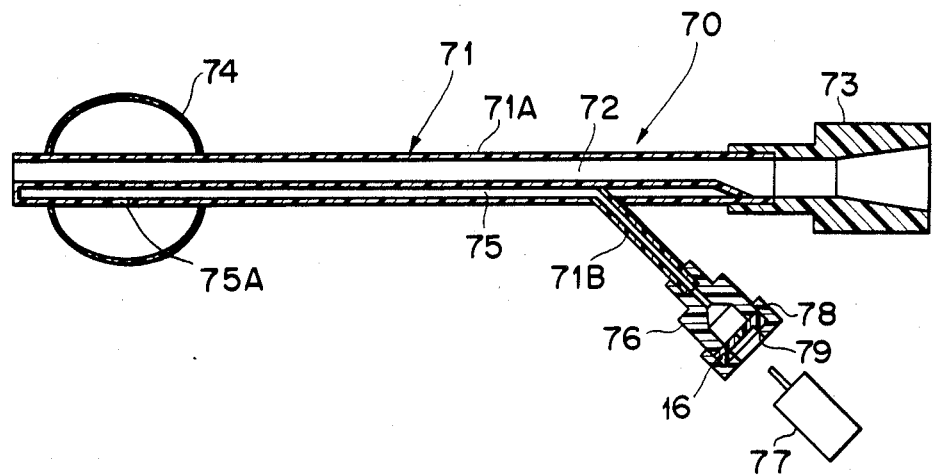
FIG. 16 is a sectional view showing the catheter with a balloon embodying the present invention.
Figure 17:
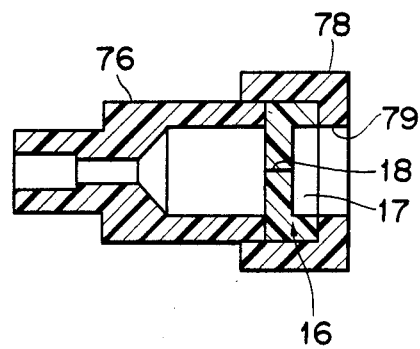
FIG. 17 is a sectional view showing the essential portions in FIG. 16 being taken out.

FIG. 16 is the sectional view showing another embodiment of the catheter with the balloon according to the present invention, and FIG. 17 is the sectional view showing the essential portions thereof being taken out. The main body 71 of the catheter with the balloon 70 comprises a flexible straight portion 71A and a branch portion 71B branchingly provided at the proximal end of the straight portion 71A. The straight portion 71A of the main body 71 has a main path 72 penetrating through the straight portion 71A from the proximal end to the forward end thereof. The main path 72 can receive therein a guide wire capable of introducing the catheter with the balloon into the blood-vessel and can allow an agent or the like to circulate therethrough. In addition, a main hub 73 is secured to the proximal end portion of the straight portion 71A. A baloon 74 made of an elastomeric material, which is expandable from a shrunk state, is provided on the outer peripheral portion of the forward end of the straight portion 71A. The straight portion 71A and the branch portion 71B of the main body 71 is formed with an auxiliary path 75 extending from the proximal end of the branch portion 71B and communicating the branch portion 71B with an internal space of the balloon 74 through a communication port 75A. The branch portion 71B of the main body 71 is connected thereto with an auxiliary hub 76 communicated with the auxiliary path 75. Secured to the opening at the proximal end of the auxiliary hub 76 is the valve body 16 for receiving therein a syringe 77 capable of pouring the liquid for expanding the balloon. The valve body 16 is held by a cap 78 coupled to the auxiliary hub 76. Additionally, a path 79 is formed in the cap 78.

In the catheter with the balloon for the blood-vessel, the main body of said catheter is made of polyurethane, polyethylene or the like, and the balloon is made of polyvinyl chloride, silicone rubber.

The foregoing is a description of the examples of the case where the catheter with the balloon according to the present invention is applied to the blood-vessel. When the catheter with the balloon according to the present invention is applied to the urethra, it is identical in arrangement with the catheter with the balloon for the blood-vessel except that a forward end portion of the main body of the catheter has a semispherical block end and a side hole communicating the main path in the main body of the catheter with the exterior is provided in the side wall of the forward end portion.

In the catheter with the balloon for the urethra, the main body of said catheter is made of latex rubber, silicone rubber, polyvinyl chloride or the like, and the balloon is made of latex rubber, silicone rubber or the like.

Description will hereunder be given of action of the above embodiments.

With the catheter with the balloon for the blood-vessel, firstly, prior to the use of the catheter with the balloon 70, the hollow needle, having inserted therethrough the inner needle, penetrates the skin and is introduced into the blood-vessel. Thereafter, the guide wire is inserted through the hollow needle, from which the inner needle has been removed, and thereupon, the hollow needle is removed, leaving the guide wire behind. Subsequently, the catheter introducer is inserted into the blood-vessel through the utilization of the guide wire to remain in the blood-vessel. After the guide wire is withdrawn, the catheter with the balloon 70 is introduced into the blood-vessel under the guidance of the guide wire, and the balloon 74 being in the shrunk state is led to a predetermined position in the blood-vessel where the balloon is to be expanded.

Subsequently, the syringe 77 capable of pouring the liquid for expanding the balloon such as physiological salt-water is inserted through the path 79 of the cap 78, the slits 17 and 18 of the valve body 16 and the crossing portions 19 thereof, and the liquid for expanding the baloon is poured into the auxiliary path 75 by means of the syringe 77. During pouring of the liquid for expanding the balloon into the auxiliary path 75, the slits 17 and 18 of the valve body 16 come into close surface-to-surface contact with the outer periphery of the syringe 77 with no gaps being formed, whereby the liquid-tight state is maintained, so that the liquid for expanding the balloon can be prevented from leaking.

When the balloon is expanded to a state of a predetermined degree of expansion by the liquid for expanding the balloon as described above, the syringe 77 is removed, and a predetermined working as described above is performed by the balloon 74 thus expanded. To remove the syringe 77, the syringe 77 is withdrawn from the slits 17 and 18 of the valve body 16, and simultaneously, the slits 17 and 18 form a perfect seal, so that the liquid for expanding the baloon can be prevented from flowing out. Furthermore, since each of the slits 17 and 18 of the valve body 16 is open only to one or the other of the end faces of the valve body 16, the force of restitution to the closed state is strong when the syringe 77 is withdrawn, and no conversely opening action at the end face opposite thereto is made. Additionally, in the valve body 16, from which the syringe 77 has been removed, each of the slits 17 and 18 is not open to one or the other of the end faces of the valve body 16, whereby the pressure resistance of the valve body 16 to the pressure of the liquid for expanding the balloon acting on the end faces of the valve body 16 is high, so that the stably closed state can be maintained with the slits not being deformed by the pressure of the liquid for expanding the balloon.

With the catheter with the balloon for the urethra, the catheter with the balloon is directly inserted into the urethra. However, when the inserting resistance is high because of the large outer diameter of the catheter with the balloon, a core metal is inserted through the main path of the catheter with the balloon and the catheter with the balloon is inserted along with the core metal into the urethra.

Figure 18:
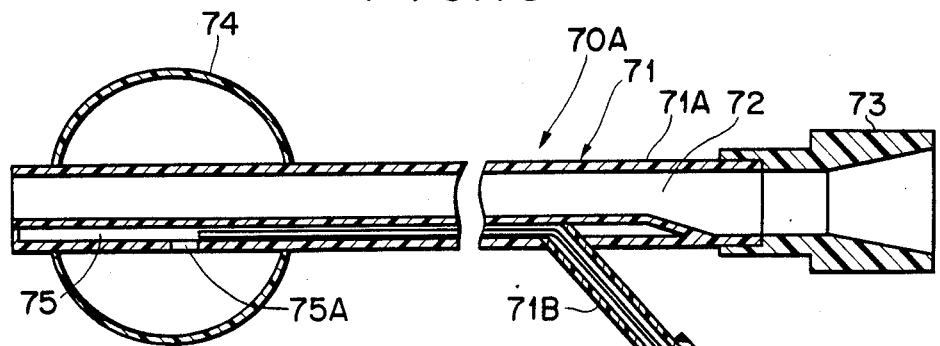
FIG. 18 is a sectional view showing the catheter with a balloon embodying the present invention.
Figure 19:
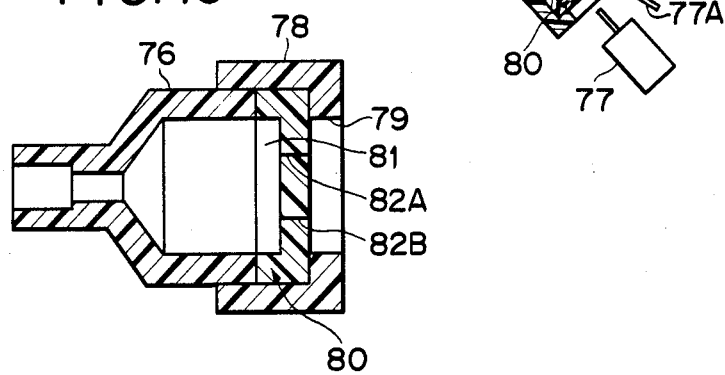
FIG. 19 is a sectional view showing the essential portions in FIG. 18 being taken out.
Figure 20A:
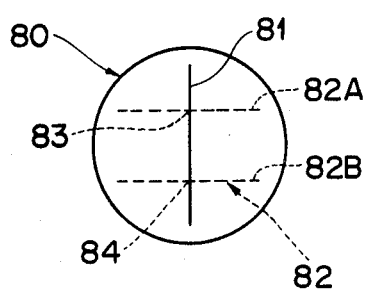
FIGS. 20(A) and 20(B) are explanatory views showing the valve body in FIG. 18 being taken out.
Figure 20B:
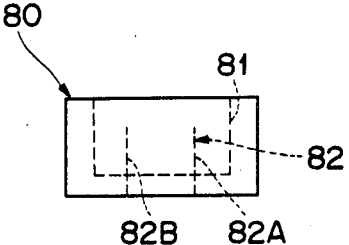

FIG. 18 is the sectional view showing a further embodiment of the catheter with the balloon 70A according to the present invention, and FIG. 19 is the sectional view showing the essential portions thereof being taken out. In this catheter with the balloon 70A, the same reference numerals are used to designate same parts as those in the catheter with the baloon 70 shown in the embodiment in FIG. 16, so that detailed description will be omitted. The following is the difference between this catheter with the balloon 70A and the aforesaid catheter with the balloon 70. Namely, secured to the auxiliary path 76 of the catheter with the balloon 70A is a valve body 80 as shown in FIGS. 20(A) and 20(B) through the cap 78. This valve body 80 is formed with a first slit 81, which is open to one of the end faces of the valve body 80, an end face not exposed to the external space and disposed at the forward end opposite to the auxiliary path 75 and consists of one slit portion, and a second slit 82, which is open to the other of the end faces of the valve body 80, an end face exposed to the external space and disposed at the rear end as viewed from the auxiliary path 75 and consists of two slit portions 82A and 82B not crossing each other. The first slit 81 and the second slit 82 cut across each other at two positions in the valve body 80. More specifically, the first slit 81 and the slit portion 82A cross each other at a crossing portion 83, whereby the syringe 77 capable of pouring the liquid for expanding the balloon is made insertable through this crossing portion 83. The first slit 81 and the slit portion 82B cross each other at a crossing portion 84, whereby a small diameter tube 77A is made insertable through this crossing portion 84. The small diameter tube 77A is inserted through the crossing portion 84 of the valve body 80 and reaches a position where a communicating port 75A of the auxiliary path 75 is provided, and can discharge air from the balloon 74 and the auxiliary path 75 to outside when the balloon 74 is expanded by the liquid for expanding the balloon.

As described above, the valve body 80 is formed with the second slit 82 consisting of the two slit portions 82A and 82B at the end face of the rear end thereof as viewed from the auxiliary path 75, exposed to the external space, so that the syringe 77 and the small diameter tube 77A can be quickly inserted through the slit portions 82A and 82B.

The valve body 80 is made of a flexible and elastomeric material similar to that of the aforesaid valve body 16.

Description will hereunder be given of action of the above embodiment.

With the catheter for the blood-vessel, firstly, similarly to the catheter with the balloon 70 in the preceding embodiment, the catheter with the balloon 70A is introduced into the blood-vessel by means of the catheter introducer, and the balloon 74 being in the shrunk state is led to a predetermined position in the blood-vessel where the balloon 74 is to be expanded.

Subsequently, the small diameter tube 77A is inserted through the auxiliary path 75, penetrating through the path 79 of the cap 78, the slit portion 82B and the slit 81 of the valve body 80 and the crossing portion 84 therebetween, and the forward end portion of the small diameter tube 77A is inserted to a position where the communicating port 75A is provided. Subsequently, the syringe 77 capable of pouring the liquid for expanding the baloon such as physiological salt-water is inserted through the path 79 of the cap 78, the slit portion 82A and the slit 81 of the valve body 80 and the crossing portion 83 therebetween. The liquid for expanding the balloon is poured into the auxiliary path 75 and the balloon 74 by means of the syringe 77, and air in the auxiliary path 75 and the balloon is discharged to outside through the small diameter tube 77A. During pouring of this liquid for expanding the balloon, the slits 81 and 82 and the slit portions 82A and 82B of the valve body 80 come into close surface-to-surface contact with the outer periphery of the small diameter tube 77A with no gaps being formed, whereby the liquid-tight state is maintained, so that the liquid for expanding the balloon can be prevented from leaking.

Subsequent to the discharge of air from the small diameter tube 77A, the completion of discharge of air in the auxiliary path 75 and the balloon 74 is ascertained by the discharge of the liquid for expanding the balloon from the small diameter tube 77A, and thereupon, the small diameter tube 77A is removed from the auxiliary path 75 and the valve body 80. Thereafter, the liquid for expanding the balloon is continuously poured into the auxiliary path 75 and the balloon 74 by means of the syringe 77. Upon expansion of the balloon 74 to a state of a predetermined degree of expansion only by the liquid for expanding the balloon from the syringe 77 is removed, and the predetermined working as described above is performed by means of the balloon 74 thus expanded. To remove the syringe 77 and the small diameter tube 77A, the syringe 77 or the small diameter tube 77A is withdrawn from the valve body 80, and simultaneously, the slits 81 and 82 form a perfectly closed seal, so that the liquid for expanding the balloon can be prevented from flowing out. Since each of the slits 81 and 82 of the valve body 80 is open only to one or the other of the end faces of the valve body 80, the force of restitution to the closed state is strong when the syringe 77 or the small diameter tube 77A is removed, and no conversely opening action at the end face opposite thereto is made. In the valve body 80 from which the syringe 77 or the small diameter tube 77A is removed, each of the slits 81 and 82 is open to only one or the other of the end faces, whereby the pressure resistance to the pressure of the liquid for expanding the balloon acting on the end faces of the valve body 80 is high, so that the stably closed state can be maintained with the slits being not deformed by the pressure of the liquid for expanding the balloon.

In addition, in the above embodiment, the use of the valve body 80 having the two crossing portions 83 and 84 has been described. However, the present invention may adopt such an arrangement so that the first slit and the second slit cross at three or more positions in the valve body and two or more small diameter tubes different from one another are made insertable through two or more slit crossing portions in parallel to one another.

The valve bodies 16 and 80 used in the catheters in the above embodiments come into close surface-to-surface contact with the outer periphery of the small diameter tube or the syringe with no gaps being formed even when the small diameter tube or the syringe is comparatively small or comparatively large in outer diameter, so that each of the valve bodies 16 and 80 can be closely attached to the small diameter tube or the syringe in the liquid-tight state.

In the above embodiments, the use of the catheters with the balloon 70 and 70A for the blood-vessel has been described, however, the catheter with the balloon according to the present invention may be used as other catheters such as the catheter for the urethra.

Figure 21:
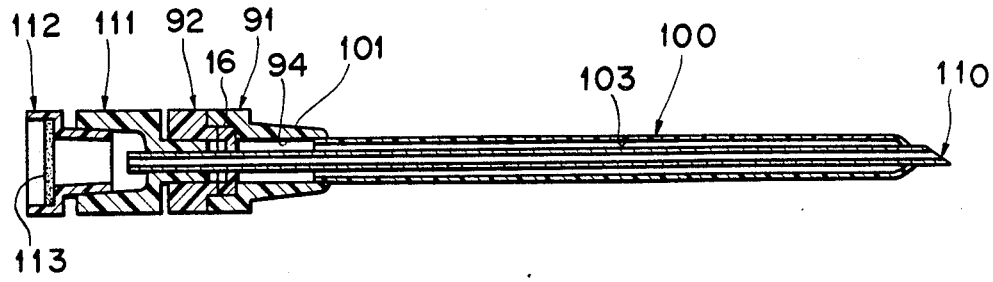
FIG. 21 is a sectional view showing a puncture needle with the valve body embodying the present invention.
Figure 22:
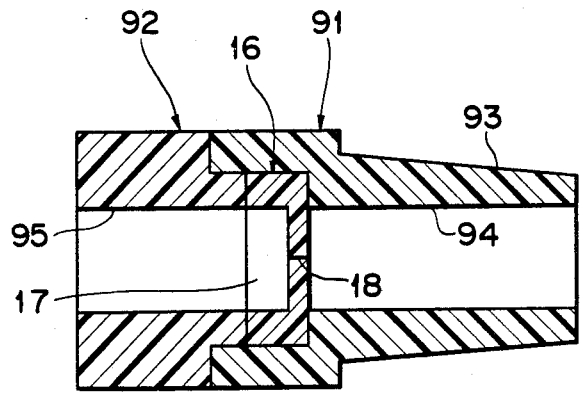
FIG. 22 is a sectional view showing a tubular hub of the puncture needle with the valve body shown in FIG. 21.

FIG. 21 is the sectional view showing the puncture needle with the valve body embodying the present invention, and FIG. 22 is the sectional view showing a tubular hub being taken out. In this embodiment, the valve body 16 is clamped between a plug 91 constituting a tubular member hub 101 and a cap 92 coupled to one end of the plug 91 in a manner to block a path in the tubular member hub 101. The tubular member hub 101 is solidly secured to one end of a tubular member 100 made of plastics and has a path 94 communicated with the interior of the tubular member 100. Further, coupled to the proximal end of the tubular member hub 101 is an inner needle hub 111 solidly secured to the proximal end portion of an inner needle 110 extending through the path 94 in the tubular member hub 101, being insertable through a path 103 in the tubular member 100 and positioning a cutting edge thereof at the other end of the tubular member 100. Coupled to an opening end of the inner needle hub 111 as necessary is a vent plug 112 provided with a membrane filter 113 which passes therethrough air, but not blood, or a filter 113 made of a sintered material. The filter 113 may be previously integrally embedded in the inner needly hub 111.

Description will hereunder be given of action of the puncture needle with the valve body in the above embodiment. Firstly, in the conditions where the inner needle hub 111 is coupled to the tubular member hub 101 as shown in FIG. 21, the tubular member 100 having inserted therethrough the inner needle 110 penetrates the skin and is introduced into the blood-vessel. At this time, the blood flows into the inner needle hub 111, passing through the inner needle 110, whereby it is ascertained that the inner needle 110 has been introduced into the blood-vessel. However, since the vent plug 112 provided at the proximal end of the inner needle hub 111 has the blood-leak resistant filter 113, the blood flow is stopped at the position of the filter 113. When the vent plug 112 is not in use, the opening at the proximal end of the inner needle hub 111 may be pressed with a finger to stop the blood leak. Subsequently, the inner needle hub 111 is supported by a finger, and the inner needle 110 is withdrawn from the tubular member 100. At this time, the inner needle 110 is in close surface-to-surface contact with the slits 17 and 18 of the valve body 16 at the crossing portion therebetween with no gaps being formed, so that the blood can be prevented from leaking through a portion where the valve body 16 and the inner needle 110 are in close contact with each other. Further, when the inner needle 110 is completely withdrawn from the tubular member 100, the valve body 16 perfectly closes the path at the crossing portion between the slits 17 and 18, so that the blood can be prevented from flowing out of the valve body 16.

In addition, in the valve body 16, each of the slits 17 and 18 is open only to one or the other of the end faces of the valve body 16, whereby the pressure resistance to the pressure acting on the end faces of the valve body 16 is high, so that the stable closed state can be maintained with the slits not being deformed by the blood pressure. The tubular member 100 is retained in the blood-vessel as described above. Thereafter, rod-like members such as a guide wire, a liquid transfusion set, a blood-transfusion set, a connector of a blood circuit for dialysis, a pour tip of a syringe and the like are inserted into the valve body 16, and connected to the path 103 in the tubular member 100. At this time, the rod-like member such as a guide wire is brought into close surface-to-surface contact with the slits 17 and 18 of the valve body 16 with no gaps being formed, whereby the liquid-tight state is maintained, so that the blood leak can be prevented.

When the aforesaid rod-like members are removed from the valve body 16, the slits 17 and 18 of the valve body 16 immediately form a perfectly closed seal, so that the blood flow out can be prevented. In addition, the slits 17 and 18 of the valve body 16 come into close surface-to-surface contact with the outer periphery of the rod-like member with no gaps being formed, even when the rod-like member to be inserted is comparatively small or comparatively large in outer diameter, so that the slits 17 and 18 can be closely attached to the rod-like member such as the guide wires different in outer diameter from each other, in the liquid-tight state.

Tests were made on the liquid-leak resistance of the puncture needle with the valve body according to the present invention. Firstly, a liquid transfusion set (TKA 400 1: manufactured by TERUMO K.K.) was connected to a flexible plastics bag (TP-10NS: manufactured by TERUMO K.K.) containing therein physiological salt-water of 1000 ml. More specifically, a spike needle made of plastics pierced the aforesaid bag, the forward end portion of an externally tapered discharge port (outer diamter: 4 mm, inner diamter: 2 mm) of a connector having an air trap portion and connected to a tube extended from the spike needle was cut away by a predetermined legth, and the forward end portion was inserted into and solidly secured to an opening at the proximal end of the tubular hub, from which the inner needle of the purncture needle with the valve body had been withdrawn as shown in FIG. 21. The aforesaid bag was the fixed at a position three meters high from the ground in such a mannner that the aforesaid discharge port did not contact the valve body in the closed state of the valve body, and tests were made on the liquid-leak resistance of the valve body to the pressure of a water column of about three meters. In addition, the valve body used is made of a silicone rubber (Q7-4735: manufactured by Dow Corning Corporation), had a thickness of 6 mm, a diameter of 8 mm and an effective diameter of 6 mm, excluding a portion supported by the tubular hub. The valve body was formed with a slit as shown in FIG. 5. The discharge port of the aforesaid connector, which was not cut as aforesaid, was inserted into and solidly secured to the opening at the proximal end of the tubular member hub, from which the inner needle had been withdrawn, the discharge port potion was inserted therethrough with the valve body, the path in the tubular member solidly secured to the tubular member hub was close, and the tests similar to the above were conducted.

In the respective test, 10 samples were used, respectively. However, in all cases, leak of physiological salt-water from the valve body was not observed. When the tubular member is actually retained in the blood-vessel, it is conceivable that the maximum blood pressure of water column of about two meters acts on the valve body. The results of the above tests proved that the puncture needle with the body according to the present invention showed a satisfactory liquid-leak resistance.

Figure 23A:
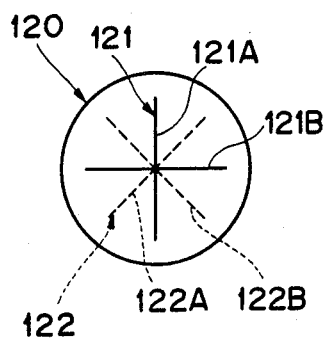
FIG. 23(A) is a plan view showing a first modification of the valve body accoding to the present invention.
Figure 23B:
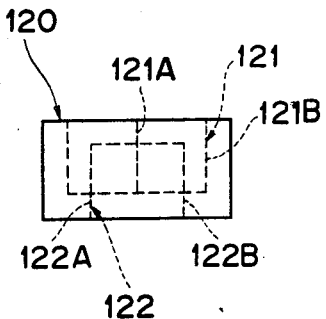
FIG. 23(B) is a side view of FIG. 23(A)

FIGS. 23(A) and 23(B) are the explanatory views showing the first modification of the valve body according to the present invention. In this valve body 120, a first slit 121 includes slit portions 121A and 121B, which cross each other, and a second slit 122, which includes crossing slit portions 122A and 122B. The first slit 121 and the second slit 122 cross each other at a single position in the valve body 120. With this valve body 120, in the conditions where the lengths of the respective slits 121 and 122 are comparatively decreased, deforming powers of the slits 121 and 122 can be increased, so that a rod-like member having a comparatively large outer diameter can be inserted through the valve body 120 being of comparatively small size.

Figure 24A:
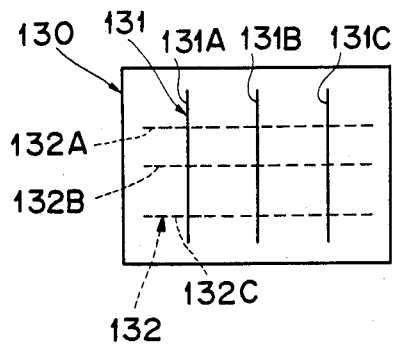
FIG. 24(A) is a plan view showing a second modification of the valve body according to the present invention.
Figure 24B:
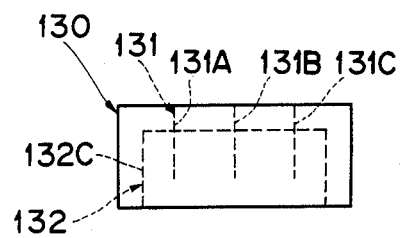
FIG. 24(B) is a side view of FIG. 24(A)

FIGS. 24(A) and 24(B) are the explanatory views showing the second modification of the valve body according to the present invention. In this valve body 130, a first slit 131 includes slit portions 131A, 131B and 131C, which do not cross one another, and a second slit 132 includes slit portions 132A, 132B and 132C, which do not cross one another. The first slit 131 and the second slit 132 cross each other at nine positions in the valve body 130. In consequence, with this valve body 130, nine rod-like members can be simultaneously inserted thereinto and held therein at the maximum.

Figure 25A:
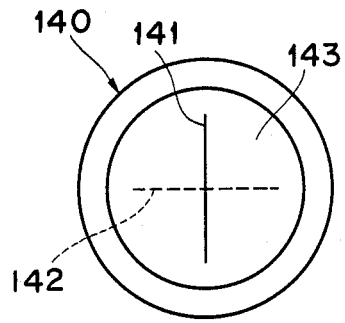
FIG. 25(A) is a plan view showing a third modification of the valve body according to the present invention.
Figure 25B:
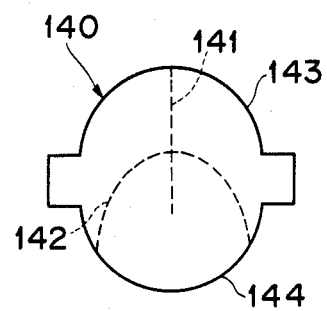
FIG. 25(B) is a side view of FIG. 25(A)

FIGS. 25(A) and 25(B) are the explanatory views showing the third modification of the valve body according to the present invention. This valve body has a first slit 141 and a second slit 142, and the end faces 143 and 144 thereof are convex. In consequence, in this valve body 140, the blood pressures acting on the end faces thereof are directed to the central portion of the valve body 140, so that the closed seal of the valve body 140 and the liquid-tight state of the rod-like member can be more reliably attained.

Figure 26:
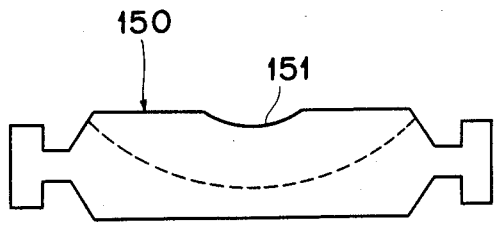
FIG. 26 is a side view showing a modification of the valve body according to the present invention

A recess 151 having a suitable size is formed at the central portion of one of the end faces of the valve body 150 as shown in FIG. 26, whereby the tip end of the rod-like member such as the guide wire is guided toward the center of the valve body, thus facilitating the insertion of the rod-like member.

SPECIFIC ADVANTAGES OF THE INVENTION

As has been described hereinabove, according to the present invention, a medical instrument comprises: a main body provided therethrough with a path, through which a rod-like member is insertable or drawable; and a valve body provided in the path of the main body, maintaining at least a liquid-tight state with the rod-like member when opened by the rod-like member, and closing the path at least liquid tight when the rod-like member is absent from the path. The valve body has two end faces in the path, a first slit openable in one of the end faces and a second slit openable in the other of the end faces. The first slit and the second slit cross each other in the valve body, and rod-like member is insertable or drawable at the crossing of the slits. In consequence, the rod-like members having outer diameters widely varied are inserted into and held in the path of the main body in the liquid-tight state to thereby reliably prevent blood leakage, and the blood flowout is reliably prevented when the rod-like members are suddenly withdrawn from the path of the main body. Further, a the single valve body is provided, so that the construction can be simplified.

Furthermore, in the medical instrument according to the present invention, the valve body is made of a flexible and elastomeric material, whereby the slits of the valve body come into close surface-to-surface contact with the outer peripheral portion of the rod-like member or members, so that the liquid-tight state between the valve body and the rod-like member or members can be made reliable.

Still further, in the medical instrument according to the present invention, the aforesaid first slit includes a plurality of slit portions crossing one another, the aforesaid second slit includes a plurality of slit portions crossing one another, and the first slit and the second slit cross at a single position in the valve body, whereby, in the conditions where the lengths of the respective slits are made comparatively small, the deforming powers of the respective slits can be increased, so that the rod-like member being comparatively large in outer diameter can be inserted into and held in the valve body being of a comparatively small size.

Additionally, in the medical instrument according to the present invention, the first slit includes a plurality of the slit portions not crossing one another, the second slit includes a plurality of slit portions not crossing one another, and the first slit and the second slit cross at a plurality of positions in the valve body, whereby in the positions of insertion of the rod-like member in the valve body are given in plural number, so that a plurality of rod-like members can be inserted simultaneously.

In the valve member according to the present invention, the end faces thereof are convex, whereby the fluid pressures acting on the end faces are directed toward the central portion of the valve body, so that the closed state of the valve body and the liquid-tight state to the rod-like member or members can be reliably attained.

What is claimed is:

1. A medical instrument comprising:
   a main body having a path extending therethrough, and wherein a rod-like member is insertable or drawable through said path; and
   a valve body provided in said path of the main body for maintaining at least a liquid-tight seal with said rod-like member when said valve body is opened by said rod-like member being passed through said valve body and through said path, and for closing said path at least in a liquid-tight state when said rod-like member is absent from said path, said valve body being made of a flexible and elastic material and being a single integral member;
   said valve body having two end faces in said path;
   said valve body further having a first slit openable in only one of said end faces and a second slit openable only in the other of said end faces, said first and second slits being oriented at an angle to each other;
   said first slit and said second slit each extending only partly through said valve body and crossing each other within said valve body, said first and second slits intersecting each other at points below or between said end faces of said valve body but not at said end faces of said valve body; and
   said rod-like member being insertable or drawable through said slits at the crossing of said slits.

2. The medical instrument of claim 1, further comprising a multiple port valve means coupled to a plurality of sources of liquid flow; and wherein said main body includes a flexible tube having an opening at one end thereof which communicates with said path, and said flexible tube having another opening at the other end thereof which is coupled to said valve means for switching between a plurality of flow courses.

3. The medical instrument of claim 1, wherein said main body comprises:
   a tubular member having a proximal end and defining a flow path;
   a tubular member hub solidly secured to the proximal end of said tubular member, and defining a path which communicates with said flow path formed in said tubular member, said valve body being provided in said path of said tubular member hub;
   a dilator tube insertable or drawable through said paths in both said tubular member and said tubular member hub, and having a forward end portion which is positioned at the other end of said tubular member when inserted; and
   a dilator hub solidly secured to a proximal end of said dilator tube and capable of being coupled to said tubular member hub.

4. The medical instrument of claim 1, wherein said main body is provided at one end portion thereof with a catheter which communicates with said path of said main body, and is provided at an opening portion of the proximal end thereof with said valve body.

5. The medical instrument of claim 1, wherein said main body is a tubular member and comprises a connector at at least one end thereof for connecting to a tubular portion of another medical instrument.

6. The medical instrument of claim 1, further comprising:
   tubular means defining a flow path;
   said main body being coupled to said tubular means such that said path of said main body is in communication with said flow path defined by said tubular means with said path of said main body intersecting said flow path at an angle; and
   said main body further including a guide portion coupled to said path of said main body for guiding insertion of said rod-like member to said valve body in said path of said main body.

7. The medical instrument of claim 1, wherein:
   said main body includes a catheter having a main path and a balloon provided on a peripheral portion at the forward end of said catheter;
   said catheter has an auxiliary path extending from the proximal end to the forward end thereof and which communicates with a space in said balloon;
   a balloon expanding liquid being pourable into a space in said balloon by means of a pouring device; and
   said valve body is provided at an opening portion of said auxiliary path.

8. The medical instrument of claim 1, wherein:
   said main body comprises a tubular member, a tubular member hub solidly secured to one end of said tubular member and having a path which communicates with the interior of said tubular member, an inner needle passing through a path of said tubular member and which is insertable or drawable into said tubular member and having a needle point positioned at the other end of said tubular member when inserted in said tubular member, and an inner needle hub capable of being coupled to said tubular hub and solidly secured to the proximal end of said inner needle; and said valve body is provided in the path of said tubular member hub.

9. The medical instrument of claim 1, wherein said valve body is a disk-like body.

10. The medical instrument of claim 1, wherein, in said valve body, said first slit comprises a plurality of slit portions crossing one another, said second slit comprises a plurality of slit portions crossing one another, and said first slit portions and said second slit portions cross each other at a single position in the inner sides thereof.

11. The medical instrument of claim 1, wherein, in said valve body, said first slit comprises a plurality of slit portions not crossing one another, said second slit comprises a plurality of slit portions not crossing one another, and said first slit and said second slit cross each other at a plurality of positions in the inner sides thereof.

12. The medical instrument of claim 1, wherein said valve body has at least one convex face.

13. The medical instrument of claim 1, wherein said slit is formed axially of said valve body, and said main body is cylindrical.

14. The medical instrument of claim 2, wherein said main body comprises:
   a tubular member;
   a tubular member hub solidly secured to the proximal end of said tubular member, having a path communicated with a path formed in said tubular member and provided in said path with said valve body;
   a dilator tube insertable or drawable through said paths both in said tubular member and said tubular member hub having the forward end portion thereof positioned at the other end of said tubular member when inserted; and
   a dilator hub solidly secured to the proximal end of said dilator tube and capable of being coupled to said tubular member hub.

15. The medical instrument of claim 1, wherein said first and second slits overlap each other so as together define said path as a substantially straight, continuous axial path between said end faces of said valve body, whereby a continuous rod-like member is insertable through said path.

* * * * *

UNITED STATES PATENT AND TRADEMARK OFFICE
CERTIFICATE OF CORRECTION

PATENT NO. : 4,610,665
DATED : September 9, 1986
INVENTOR(S) : A. MATSUMOTO et al It is certified that error appears in the above-identified patent and that said Letters Patent is hereby corrected as shown below:

Column 2, line 49, "communicated, and" should read -- communicated with --.

Column 2, line 50, "of with" should read -- of, and --.

Column 3, line 66, "the" (first occurrence) should read -- a --.

Column 6, line 11, "the" should read -- a --.

Column 6, line 18, "as so on" should be deleted.

Column 13, line 60, "baloon" should read -- balloon --.

Column 15, line 13, "baloon" should read -- balloon --.

Column 17, line 51, "the fixed" should read -- then fixed --.

Signed and Sealed this

Seventeenth Day of May, 1988

*Attest:*

DONALD J. QUIGG

*Attesting Officer*   *Commissioner of Patents and Trademarks*